United States Patent [19]

Jacobs

[11] 4,131,660
[45] Dec. 26, 1978

[54] METHOD OF EVALUATING SCORCH IN FLEXIBLE POLYURETHANE FOAM

[75] Inventor: Barry A. Jacobs, Bethel, Conn.

[73] Assignee: Stauffer Chemical Company, Westport, Conn.

[21] Appl. No.: 854,288

[22] Filed: Nov. 23, 1977

[51] Int. Cl.² .............................................. B29D 27/04
[52] U.S. Cl. ..................................... 264/26; 73/15 R; 73/159; 264/40.1; 264/54; 521/107; 521/906
[58] Field of Search ......................... 264/26, 54, 40.1, ; 260/2.5 BB; 73/15 R, 159

[56] References Cited

U.S. PATENT DOCUMENTS

| | | | |
|---|---|---|---|
| 3,255,129 | 6/1966 | Ferrari | 260/2.5 BB |
| 3,294,879 | 12/1966 | Jacobs | 264/26 |
| 3,299,147 | 1/1967 | O'Shea | 260/2.5 BB X |
| 3,364,153 | 1/1968 | Larrison | 260/2.5 BB X |
| 3,429,837 | 2/1969 | Langrish et al. | 260/2.5 BB |
| 3,567,664 | 3/1971 | Haring | 260/2.5 BB |
| 3,714,077 | 1/1973 | Cobbledick et al. | 260/2.5 BB X |
| 3,718,611 | 2/1973 | Maxey et al. | 260/2.5 BB X |
| 3,772,218 | 11/1973 | Lamplugh et al. | 260/2.5 BB |
| 3,847,843 | 11/1974 | Dany et al. | 260/2.5 BB |

OTHER PUBLICATIONS

Lanigan, W. L. "Microwave Curing of Flexible Polyurethane Foam Mouldings", in *British Plastics*, Oct. 1963, pp. 562–565.

*Primary Examiner*—Philip Anderson
*Attorney, Agent, or Firm*—William R. Robinson

[57] ABSTRACT

A method of evaluating the probability of scorch in flame retarded flexible polyurethane foam without preparing a large quantity of foam is described. A microwave oven is utilized to heat a foam sample pursuant to the invention. The method is useful to predict the probability that flame retarded foam will scorch on curing and therefore can be used to avoid damage to large commercial quantities of foam. The method can also be used to screen flame retardants for polyurethane foams.

1 Claim, No Drawings

4,131,660

METHOD OF EVALUATING SCORCH IN FLEXIBLE POLYURETHANE FOAM

BACKGROUND OF THE INVENTION

1. Field of the Invention

This invention relates, in general, to a method of evaluating scorch in flexible polyurethane foams and particularly concerns a method of predicting the probability that flame retarded flexible polyurethane foam will scorch on curing. The method can also be used to screen flame retardants for polyurethane foams.

2. The Prior Art

The use of flame retardants in polyurethane foams is well known. Many flame retardants, however, cause the foams to scorch during the foaming reaction. In other cases, flame retarded foams can scorch during the first few hours of storage after the foaming process. This is especially likely when the new foam buns are stacked and heat transfer from the center of the buns is inhibited. Scorch not only reduces the aesthetic quality of the foam by discoloring it, but also can cause degradation of the physical properties.

It has been very difficult in the past to assess the scorch potential of flame retardants in the laboratory. Generally the small size of the foam bun produced in the laboratory allows a rapid dissipation of heat to occur, and except in the case of the least thermally stable materials any scorching or discoloration is usually minimized or undetectable. Even foam buns prepared in 1.5' × 1.5' × 3' insulated boxes do not reproducibly show scorch.

In the literature, several small scale methods for determining scorch are discussed. U.S. Pat. No. 2,915,496 discloses the use of very high water levels to produce large exotherms. Long cure cycles at elevated temperatures in ovens are disclosed in U.S. Patent No. 3,281,379. In U.S. Pat. No. 3,281,379 measurement of the induction time required for phenol oxidation is discussed. The incorporation of additives to the foam to catalyze free radical reactions is disclosed in British Pat. No. 1,407,244. Each of these methods have inherent shortcomings such as extended oven exposure times or the need to make large quantities of foam. Above all, correlation with actual commercial production has been poor. These problems have been overcome by the present invention.

SUMMARY OF THE INVENTION

In accordance with the present invention a method is provided wherein a bench scale test which correlates well with scorching conditions found in actual commercial production has been developed. The test can be performed in less than one hour and a minimum quantity of foam is required.

It has been found that the use of microwave radiant energy provides a unique method of inducing scorch in small foam samples by simulating temperature conditions which occur in production quantities of foam. This is because microwaves excite the foam molecules uniformly and the friction thereby generated heats the foam bun from the inside out. Uniformity of heating is not easily reproduced in small foam samples by conductive heating due to the insulating properties of urethane foams. When flexible urethane foam is made in large quantities, the internal bun temperature may reach 150° C. to 170° C. and remain there for 15 to 20 hours. In order to reproduce this internal temperature with conductive heating of a test bun, the outside of the bun will char before the inside reaches 150° C. to 170° C. Thus, simulation of such uniform heating as achieved in the present invention is critical to achievement of reproducible results that correlate well with commercial production conditions.

DETAILED DESCRIPTION OF THE INVENTION

The method of the present invention comprises preparing a foam formulation and curing the foam under carefully controlled conditions in a microwave oven.

After the foam formulation is mixed, it is generally poured into a container and allowed to rise. The internal temperature of the foam is allowed to rise to from about 120° C. to about 180° C. When the foam reaches a preselected temperature within that range, it is placed in the microwave oven and heated for about two minutes to about thirty minutes at a radiant energy from about 2.5 to about 7 kilocalories per minute.

One skilled in the art can determine the optimum radiant energy and time pursuant to the foregoing paragraph on the basis of the nature of the foam formulation. It is critical, however, for purposes of reproducibility, that the same radiant energy and time be used for repetitive tests on the same foam formulations with the same or different flame retardants.

The microwave oven is preferably operated by an electrical source having a constant voltage. A timer of improved accuracy over the standard oven timer is also preferred.

Calibration of the oven is required to ensure that uniform radiant energy is applied to successive foam buns. This calibration can be performed by determining the temperature rise of water heated in the oven at various power settings. A standard quantity of water is used and its temperature is measured prior to heating in the oven. The water is then placed in the oven and heated for a fixed period of time. At the end of this time, the water temperature is measured and the heat rise calculated. This procedure is repeated for various power settings and a calibration curve of temperature rise versus power setting is prepared. The radiant energy can be calculated by the equation:

$$R = \Delta TW/t$$

Where:
  $R$ = radiant energy in calories per minute
  $\Delta T$ = temperature change in ° C.
  $W$ = weight of water in grams
  $t$ = time in minutes After the foam bun is heated for a preselected time, it is removed from the oven and allowed to cure at room temperature. The foam bun is then sliced and evaluated for scorch.

The scorch of the foams of the present invention can be evaluated by numerous recognized methods as set forth, for example, in *Principles of Color Technology*, Fred W. Billinger, Jr. and Max Saltzman (Wiley Interscience, 1966)

In the experimental work on the present invention, a Hunter colormeter was utilized to measure color differences pursuant to the color-difference formula:

$$\Delta E \text{ (Hunter)} = (\Delta L^2 + \Delta a^2 + \Delta b^2)^{\frac{1}{2}}$$

Where:
  $\Delta E$ (Hunter) = color difference

ΔL = lightness compared to standard
Δa = redness, if positive, or greeness, if negative, compared to a standard
Δb = yellowness, if positive, or blueness, if negative, compared to a standard All of the values for L, a and b are calculated within the Hunter instrument by electrical means and read directly from its dials. The most commonly used standard of color comparison is a pure white sample. A white tile was used in the experimental work on the present invention.

The present invention will be more fully illustrated in the Examples which follow.

EXAMPLE I

An all water-blown, low density foam formulation was prepared with the following constituents:

| | | |
|---|---|---|
| Niax 16-46 Polyol | 300.0 | grams |
| Hylene TM Isocyanate | 183.1 | |
| Index | (110) | |
| Flame Retardant - tris (dichloropropyl)phosphate | 24 | |
| Water | 15.0 | |
| L-5720 Silicone | 3.3 | |
| Dabco 33/LV | 0.9 | |
| Niax ESN Amine Catalyst | 0.6 | |
| 50% Stannous Octoate | 1.2 | |

This foam formulation was selected since it generates a very high internal bun temperature. No auxiliary blowing agents which can modify the exotherm were incorporated.

After mixing, the incipient foam was poured into a 12" × 12" × 5.5" cardboard box, and allowed to rise freely. At the completion of rise, a thermocouple, connnected to a multipoint recorder, was inserted into the middle of the bun. When the internal bun temperature reached 150° C., the thermocouple was removed and the foam placed into a Litton Model 414 microwave oven, and heated for four minutes.

In order to ensure a uniform heating of all foam buns, the microwave oven was powered by an electrical source whose voltage was maintained at a constant value. A Gralab timer was used in place of the built in oven timer. The particular oven used in these studies was of variable power. It was calibrated to ensure that uniform radiant energy was being applied to the foam bun on a day-to-day basis. This calibration was performed by ascertaining the temperature rise of water heated in the oven at various power settings. For this purpose, the power adjustment knob was arbitrarily divided into 14 settings where 1 was the maximum heating rate.

A standard quantity of water (350 g) was placed in a 1000 ml beaker, and its temperature measured. Then, the beaker was placed in the oven and heated for 4 minutes at a particular setting. At the end of this time, the beaker was quickly removed and the temperature determined again and the heat rise calculated. This was repeated twice. In this way, a curve of temperature rise versus power setting was obtained. Linear regression of the data indicated that the square of the correlation coefficient was 0.978, where 1.0 indicates a perfect fit of the data to the straight line whose equation is:

$$\Delta T = -4.28° \text{ PS} + 75.84°$$

where ΔT is temperature rise
PS is power setting

We found that a setting of 6, which corresponds to a ΔT of 50° C., was desirable since a foam containing no flame retardant did not discolor, while one containing tris (dichloropropyl) phosphate showed a barely perceptible yellow color. This gave conditions which could induce scorch, but still maintain the commercial experience of slight or no discoloration when tris (dichloropropyl) phosphate is the flame retardant. After the foam bun was heated for the four minute period, it was removed from the oven, the thermocouple was replaced, and the foam was allowed to cure at room temperature for 30 minutes. The foam bun was then sliced in the center perpendicular to the direction of rise and examined for evidence of scorch. Because of the difficulty in visually assessing small differences in the degree of scorching, a 1" thick slice was cut from the upper half of the bun, and a 2" × 2" sample was removed from the center of the slice. A Hunter colormeter was used to ascertain the color of each cube. A color difference of ΔE = 3.83 compared to non-flame retarded foam was found.

EXAMPLE II

Several foam samples were prepared having the same formulation as in Example I except for the flame retardant.

Firstly, five foam buns which did not contain any flame retardant were prepared and cured pursuant to Example I. The color values were randomly measured in duplicate pursuant to the procedure in Example I. The results are shown in Table I.

TABLE 1

Statistical Analysis of Non-flame Retarded Foam

| Sample | Color Difference (ΔE) |
|---|---|
| 1 | 8.28 |
| 2 | 9.26 |
| 3 | 8.87 |
| 4 | 8.55 |
| 5 | 9.07 |
| Average | 8.81 |
| Standard Deviation* | 0.39 |

*four degrees of freedom

The standard deviation of 0.39 indicated excellent agreement between the five samples. It is noteworthy that the human eye can only distinguish one ΔE unit.

Seven more foams were then prepared; each with 8 php of flame retardant. Except for the flame retardants, the formulations were the same as those used in the first part of this example. The same procedures for curing and evaluation as used in the first part of this example were repeated. ΔE was then measured using non-flame retarded foam as the standard. The results are summarized in Table II.

TABLE II

Color Differences for Various Flame Retardants

| Flame Retardant | ΔE Color Difference | Standard Deviation* |
|---|---|---|
| tris (dichloropropyl) phosphate | 3.83 | 0.56 |
| 2:1 blend of poly (chloroethyl-ethyleneoxy) phosphoric acid ester: tris (dichloropropyl) phosphate | 7.82 | 1.18 |
| Thermolin ®101 | 8.02 | 1.04 |
| Phosgard ®2XC20 | 8.93 | 0.49 |
| Experimental Flame Retardant A | 16.52 | 1.50 |
| Experimental Flame Retardant B | 41.38 | 1.40 |
| Firemaster ®T23P | 46.39 | 1.51 |

TABLE II-continued
Color Differences for Various Flame Retardants

| Flame Retardant | ΔE Color Difference | Standard Deviation* |
|---|---|---|
| | pooled standard deviation | 1.17 |

*four degrees of freedom

EXAMPLE III

Ten foam samples were prepared pursuant to the formula in Example I with the exception of the flame retardant. Five of the samples were small and were cured and evaluated according to Example I. The other five samples corresponded to each of the first five but were prepared on a large scale 200 lb./min. foam machine.

ΔE values were measured with non-flame retarded foam as the standard. The results are shown in Table III.

TABLE III
Comparative Color Differences

| | ΔE Color Differences | |
|---|---|---|
| Flame Retardant | large bun | test bun |
| 2:1 blend of poly (chloroethyl-ethyleneoxy) phosphoric acid ester: tris (dichloropropyl) phosphate | 4.78 | 7.82 |
| Experimental Flame Retardant A | 6.04 | 4.23 |
| Phosgard 2XC-20 | 10.27 | 8.93 |
| Experimental Flame Retardant B | 26.43 | 39.68 |
| Experimental Flame Retardant C | 33.79 | 35.21 |

With the exception of Experimental Flame Retardant B, all of the values lie within 2 pooled standard deviations of each other.

Having set forth the general nature and some examples of the present invention, the scope is now particularly set forth in the appended claims.

I claim:

1. A method of evaluating scorch in flame retarded flexible polyurethane foam comprising heating a flame retarded flexible polyurethane foam sample having an internal temperature from about 120° C. to about 180° C. with microwave radiant energy from about 2.5 to about 7 kilocalories per minute for from about 2 minutes to about 30 minutes, then allowing said sample to cure at room temperature followed by slicing said sample and measuring the color of the sliced surface and finally comparing that color measurement to the measured color of a sliced surface of an identically formulated and cured non-flame retarded flexible polyurethane foam.

* * * * *

UNITED STATES PATENT AND TRADEMARK OFFICE
CERTIFICATE OF CORRECTION

PATENT NO. : 4,131,660
DATED : Dec. 26, 1978
INVENTOR(S) : Barry A. Jacobs

It is certified that error appears in the above—identified patent and that said Letters Patent are hereby corrected as shown below:

Col. 3, line 65

Change equation to read:

$$\Delta T = -4.29°PS + 75.84°$$

Signed and Sealed this

Twelfth Day of June 1979

[SEAL]

Attest:

RUTH C. MASON
*Attesting Officer*

DONALD W. BANNER
*Commissioner of Patents and Trademarks*